United States Patent [19]

Nakashima et al.

[11] Patent Number: 5,017,720

[45] Date of Patent: May 21, 1991

[54] METHODS OF PRODUCING AND RESERVING ALKYLENE GLYCOL MONOSORBATES

[75] Inventors: Masahiro Nakashima; Yasuo Urata; Tetsuya Nagaie, all of Minamata, Japan

[73] Assignee: Chisso Corporation, Japan

[21] Appl. No.: 486,844

[22] Filed: Mar. 1, 1990

[30] Foreign Application Priority Data

Mar. 16, 1989 [JP] Japan ................................ 1-62090

[51] Int. Cl.$^5$ .............................................. C07C 67/26
[52] U.S. Cl. .......................................... 560/209; 560/4
[58] Field of Search ......................................... 560/209

[56] References Cited

U.S. PATENT DOCUMENTS 3,280,176 10/1966 Meier et al.

FOREIGN PATENT DOCUMENTS 1081450 5/1960 Fed. Rep. of Germany .
1248036 8/1967 Fed. Rep. of Germany .
1255104 11/1967 Fed. Rep. of Germany .
1257776 1/1968 Fed. Rep. of Germany .
43-18890 8/1968 Japan .
252448 12/1985 Japan .

Primary Examiner—Paul J. Killos
Attorney, Agent, or Firm—Leydig, Voit & Mayer

[57] ABSTRACT

The invention provides a method of producing alkylene glycol monosorbates which comprises reacting sorbic acid and an alkylene oxide having 2 to 4 carbon atoms in a certain system containing a solvent inactive to the alkylene glycol monosorbates, one or more iron catalysts and one or more compounds consisting of phenothiazines and alkylphenols, washing the obtained synthesized liquid with an aqueous (bi)carbonate solution, and then purifying the washed liquid by distillation, and a method of reserving the alkylene glycol monosorbates.

5 Claims, No Drawings

METHODS OF PRODUCING AND RESERVING ALKYLENE GLYCOL MONOSORBATES

BACKGROUND OF THE INVENTION

The present invention relates to a method of producing alkylene glycol monosorbates and a method of preserving the monosorbates.

More particularly, the present invention relates to a method of producing alkylene glycol monosorbates such as hydroxyethyl sorbate, hydroxypropyl sorbate, hydroxybutyl sorbate and the like from sorbic acid and alkylene oxides such as ethylene oxide, propylene oxide, butylene oxide and the like and to a method of reserving the alkylene glycol monosorbates.

Since alkylene glycol monosorbates have two conjugated double bonds in their structure, the compounds are expected to be used in many fields as functional monomers. However, a few methods of producing the compounds were disclosed as shown in the following and a method of preserving the compounds was not disclosed at all.

In relation to a method of producing an alkylene glycol monosorbate, a method of reacting sorbyl chloride and an alkylene diol is reported (Zh. Prikim (legirad) 46 (5) 1099–1103 and Eur. J. Med. Chem. Ther. 18 (5) 441–445 (1983)), and a method in which butanediol monoester is synthesized from sorbic acid and butanediol in the presence of an acylating agent is disclosed (Japanese Laid-Open Patent Application No. 60-252448).

In these conventional methods, the method of producing an alkylene glycol monosorbate, in which sorbyl chloride and an alkylene diol are reacted, has a problem that hydrogen chloride is produced and additional processes are required to remove it because sorbyl chloride is used as a raw material. The method has further problems that isolation of the alkylene glycol monosorbate produced is difficult and the yield is lowered. As a result, the method is not effective industrially. On the other hand, the method of producing butanediol monoester, in which sorbic acid and butanediol are reacted, has problems in that an expensive acylating agent is required and that the yield of the separated product is lowered. As a result, the method is also not effective industrially.

SUMMARY OF THE INVENTION

The object of the present invention is to solve these problems and to provide methods of producing and preserving alkylene glycol monosorbates.

The present invention provides a method of producing an alkylene glycol monosorbate, which comprises a reacting sorbic acid and an alkylene oxide having 2 to 4 carbon atoms in a system containing a solvent having a boiling point of 150° C. or less at atmospheric pressure and being insoluble or slightly soluble in water and being inactive to the alkylene glycol monosorbate (abbreviated as a solvent hereinafter), in the presence of one or more catalysts selected from the group consisting of organic acid iron salts and iron halides (abbreviated as an iron catalyst hereinafter) and one or more compounds selected from the group consisting of phenothiazines and alkylphenols (b), washing the obtained synthetic liquid with an aqueous solution of a salt selected from the group consisting of sodium carbonate, potassium carbonate, sodium bicarbonate and potassium bicarbonate (abbreviated as a (bi)carbonate hereinafter), and then (c) purifying the washed liquid by distillation.

Namely, the method of producing an alkylene glycol monosorbate, comprises a step of synthesizing the alkylene glycol monosorbate by the reaction of sorbic acid and an alkylene oxide having 2 to 4 carbon atoms in the presence of a solvent, an iron catalyst and one or more compounds selected from phenothiazines and alkylphenols at atmospheric pressure or under pressure (abbreviated as a synthetic step hereinafter), a step of removing iron hydroxide and sorbate by washing the obtained synthetic liquid containing the catalyst and unreactive sorbic acid with an aqueous solution of (bi)carbonate (abbreviated as a washing step hereinafter), and a step of purifying the washed synthetic liquid by distillation to recover the low-boiling solvent and to separate the colored high-boiling materials (abbreviated as a distillation step hereinafter).

Furthermore, the present invention provides a method of preserving an alkylene glycol monosorbate, which comprises adding one or more compounds selected from the group consisting of alkylphenols and phenothiazines to the alkylene glycol monosorbate, removing oxygen from a vessel containing the mixture by blowing inert gas, and sealing hermetically the vessel (abbreviated as stabilization process hereinafter).

DETAILED DESCRIPTION OF THE INVENTION

The following steps and a process describe the methods of the present invention in detail.

Synthetic Step

In the synthetic step, alkylene glycol monosorbate is synthesized by the reaction of an alkylene oxide and sorbic acid. The reaction of the alkylene oxide and sorbic acid is facilitated by previously dissolving, by dissolving partly or by dispersing sorbic acid in a solvent. The solvent dilutes the produced alkylene glycol monosorbate, and the transfer of the obtained liquid and the operation of the following washing step become easy. Moreover, phenothiazines or alkylphenols can be dissolved by the solvent and the reaction is effectively accelerated by the dissolution. The solvent used in this step is insoluble or slightly soluble in water and the boiling point of the solvent is 150° C. or less at atmospheric pressure. The boiling point of the solvent is very different from that of the alkylene glycol monosorbate. The solvent is inactive to the alkylene glycol monosorbate. As the solvent, at least one of aromatic hydrocarbons such as benzene, toluene, xylene and the like, and halogenated hydrocarbons such as chloroform, carbon tetrachloride, trichloroethane, trichloroethylene, tetrachloroethane, tetrachloroethylene and the like, is preferably used. Further, although it is difficult to use an aliphatic hydrocarbon or an alicyclic hydrocarbon by itself, these hydrocarbons can be used by mixing with the above aromatic hydrocarbons or halogenated hydrocarbons.

The solvent is used in an amount of preferably 0.5 to 5 parts by weight, more preferably 0.8 to 4 parts by weight based on 1 part by weight of sorbic acid. When the amount of the solvent is less than 0.5 parts by weight, it is difficult to react sorbic acid with the alkylene oxide. When the amount of the solvent is more than five parts by weight, the merits of the usage of the solvent remain unchanged. The solvent can be recycled and used after recovering in the distillation step.

Among synthetic catalysts, iron salts are effective but aluminium salts and zinc salts are scarcely effective as the catalyst. Among the iron salts of inorganic acids, iron halides are effective and the other salts such as iron sulfates or iron phosphates are not effective as the catalyst. Among the iron salts of organic acids, iron sorbate, iron benzoate, iron crotonate, iron 2-ethylbutyrate and the like can be used as the catalyst in the present invention.

Among these iron catalysts, iron sorbates are most effective catalysts. When the iron salts of organic acids other than iron sorbates are used, the purity of alkylene glycol monosorbates is in some cases lowered by organic acids released from the iron salts of organic acids. When the iron halides are used, alkylene halohydrins are produced as by-products and accumulated in the solvents, so that the purification of the solvents is required.

The iron catalysts are used in an amount of 0.005 to 0.1 parts by weight, preferably 0.01 to 0.05 parts by weight based on 1 part by weight of sorbic acid. Even if the amount of the iron catalyst is too much, the reaction of sorbic acid and an alkylene oxide is not particularly troublesome. However, it is not preferable that the amount of the iron catalysts is too much, because the consumption of the (bi)carbonate increases with the increased catalysts. When the iron catalysts are used in an amount of less than 0.005 parts by weight, it is not preferable because the reaction rate is lowered.

When the water content of the catalyst, the solvent or sorbic acid is too much, it is necessary to dry them because the alkylene oxide changes to alkylene glycol in the presence of water. However, there is no problem because it is possible to easily remove water by azeotropic distillation. For this reason, water-containing sorbic acid obtained by the production process of sorbic acid, water-containing iron hydroxides or the recovered catalysts containing water, which are cheap, can be conveniently used.

Sorbic acid or alkylene glycol monosorbates are easily polymerized in the presence of oxygen or by heat. Accordingly, high boiling compounds are produced in a high-temperature process such as the synthetic process or the distillation process, and the separation yield decreases. Thus it is required that an antioxidant or a polymerization inhibitor is added.

As the additives having the effect of the antioxidant or the polymerization inhibitor, alkyl phenols such as 2,6-di-t-butyl-p-cresol, 4,4'-isopropylidene bisphenol, o- or m-t-butyl-p-methoxyphenol, hydroquinone monomethyl ether, hydroquinone, propyl gallate and the like, and phenothiazine derivatives such as phenothiazine, 3,7-di-t-octylphenothiazine, bis-α-methylbenzylphenothiazine, 2- or 4-methoxyphenothiazine, 10-(2hydroxypropyl)phenothiazine and the like can be exemplified.

When one or more of these additives are added, the alkylene glycol monosorbate can be effectively prepared and obtained in high yield. Sorbic acid and an alkylene oxide can be reacted by any process such as, for example, batch process or continuous process.

In the batch process, a catalyst, an antioxidant or a polymerization inhibitor, sorbic acid and a solvent are put in a reactor and the mixture is stirred, while an inert gas is introduced into the reactor and the temperature of the reactor is raised under an inert atmosphere. At a temperature of 45° to 95° C., preferably 50° to 90° C., a liquid or gaseous alkylene oxide is supplied to the reactor and reacted with the mixture, and an alkylene glycol monosorbate is synthesized. Equimolecular or greater amounts of the alkylene oxide per mole of sorbic acid are required and usually 1.01 to 1.2 moles are suitable.

The synthesis of the alkylene glycol monosorbate can be conducted at atmospheric pressure. When ethylene oxide having a low boiling point is used, a slightly pressurized system can be used to advantage in the synthesis so as to use all of ethylene oxide.

Washing Step

It has been found that when the synthesized liquid is purified by distilling as it is, the heat transfer surface of a distillation apparatus is contaminated by the catalyst and the long-term operation becomes impossible, and the storage stability of the alkylene glycol monosorbate obtained by distilling becomes bad. For solving these problems, the synthesized liquid is stirred and washed in the presence of sodium or potassium (bi)carbonate at a pH value of seven or more, the aqueous layer is removed by a process such as two-layer separation, centrifugation, or filtration, and the separated oil layer is distilled.

Use of sodium hydroxide or potassium hydroxide instead of the (bi)carbonates is not preferred, because the hydrolysis of alkylene glycol monosorbate occurs and the yield of the compound is lowered. Citrate or salts of EDTA instead of the (bi)carbonates can also be used. However, as these compounds are more expensive than the (bi)carbonates, the use of these compounds are industrially not advantageous. Furthermore, phosphoric acid can be used for removing the catalyst, however, the use in the presence of unreactive sorbic acid is undesired because the sorbic acid remains in the oil layer and can not be removed.

The aqueous solution of the (bi)carbonate is usually used in a concentration from three to ten % by weight. Even though sodium or potassium salts of mineral acids are contained in the aqueous solution, there are no problems. Preferably, when the sodium or potassium salts of mineral acids are contained in the aqueous solution of the (bi)carbonate, the specific gravity of the solution becomes greater and the separation of the oil layer can be easily conducted after the washing step., As the water layer obtained after the washing step contains a precipitate of iron hydroxide and a solution of sodium or potassium sorbate, the water layer can be treated in sulfuric acid or hydrochloric acid to regenerate iron sorbate obtained, and the obtained iron sorbate can be reused as the catalyst. There are several methods for regenerating the iron sorbate. For example, the precipitate of iron hydroxide is usually dissolved in hydrochloric acid or sulfuric acid, and then mixed with sodium or potassium sorbate obtained by separation after the washing step, and the obtained iron sorbate is filtered and reused in the cycle.

Furthermore, as the filtered water can be reused for dissolving the (bi)carbonate, the amount of waste water becomes small. The filtered water has a high specific gravity because it contains the sodium or potassium salt of the mineral acid. Accordingly, the separation of the water layer and the oil layer from the synthesized liquid after neutralizing and washing becomes easy.

Distillation Step

After the washing step, the synthesized liquid contains a little water. The water is removed by the first distillation from the liquid and the solvent is recovered. High-boiling materials are then removed by the next distillation and a high-quality alkylene glycol monosorbate is produced. The distillation is preferably conducted in vacuo. Especially, after the low-boiling solvent is recovered, the alkylene glycol monosorbate is preferably distilled under as high vacuum and low temperature as possible. Since shorter retention time of the distillate is preferred, a continuous vacuum distillation apparatus having a distillation element for cutting low-boiling materials and a distillation element for cutting high-boiling materials is suitable.

After water is removed from the low-boiling solvent obtained by the distillation step, the dried solvent is circulated and reused. The high-boiling materials are removed outside the recycle system. The yield of the isolated alkylene glycol monosorbate is 90% or more, and the purity is 99% or more. The monosorbate can be obtained in high quality.

Stabilization Process

In this stabilization process, for stabilizing the polymerizable alkylene glycol monosorbate without any change of properties, oxygen is excluded and antioxidants or polymerization inhibitors are added.

For preserving the alkylene glycol monosorbate, it is placed in a vessel which can be hermetically sealed, oxygen dissolving in the above alkylene glycol monosorbate and oxygen in the atmosphere are discharged by introducing inert gas into the vessel, the antioxidants or the polymerization inhibitors are added and dissolved in the alkylene glycol monosorbate, and then the vessel is hermetically sealed. The above additives previously dissolved in high concentration in some alkylene glycol monosorbate can be added and the concentration adjusted. As the inert gas, nitrogen or argon can be used.

The additives effective as the antioxidants or the polymerization inhibitors are alkyl phenols or phenothiazines which are used in the above synthetic step. The alkyl phenols and phenothiazines are used alone, or preferably in combination. The amount to be used of the alkyl phenols is 400 to 2000 ppm and that of the phenothiazines is 50 to 300 ppm. By using these stabilizers, the alkylene glycol monosorbate can be preserved without any change of properties.

According to the methods of the present invention, it is possible to easily produce alkylene glycol monosorbates in high yields and at a low cost. Furthermore, the obtained alkylene glycol monosorbates are made stable to the preservation of long periods, and so are tolerable to severe marketing.

Accordingly, the methods of the present invention are preferable as an industrially producing method and a preserving method for the above alkylene glycol monosorbates

DESCRIPTION OF PREFERRED EMBODIMENTS

The following Examples illustrate the present invention more specifically.

EXAMPLE 1

A reactor equipped with a stirrer and a cooling condenser was charged with 45.0 kg (purity 99.6%) of sorbic acid, 45.0 kg of xylene, 1.5 kg of ferric sorbate and 0.004 kg of phenothiazine. After nitrogen gas was blown into the reactor so as to remove oxygen, the mixture was heated to a temperature of 75° C. with stirring and 24.4 kg of liquid propylene oxide was added at a rate of 160 ml/min.

The obtained synthesized liquid was cooled to 45° C. with stirring and analyzed. The rate of reaction of sorbic acid was 99.6%. An aqueous solution having a volume of 50 liters and containing about 10% of sodium chloride and 7% of sodium carbonate was added to the liquid and stirred for 30 minutes. After the stirred solution was left, an aqueous phase containing a precipitate of ferric hydroxide and a xylene phase were separated.

Then, the xylene phase was passed through a filter to separate the trace amounts of dispersed solids and then passed through a film distillation column set at 80° C. and 30 mmHg abs to remove xylene. Further, the residue was passed through a film distillation column set at 120° C. and 64.3 kg of purified propylene glycol monosorbate (a mixture of 2-hydroxypropyl sorbate and 2-hydroxy-1-methylethyl sorbate) having a purity of more than 99%, a Hazen platinum-cobalt standard (APHA) of less than 20 and a viscosity of $6 \times 10$ cp at 20° C. was obtained.

The yield of the isolated propylene glycol monosorbate based on the starting amount of sorbic acid was 94%. Four chemical tanks of 20 liters were charged with 15 kg of the purified propylene glycol monosorbate, respectively. Amounts of 6.0 g (400 ppm) of 2,6-di-t-butyl-p-cresol and 0.75 g (50 ppm) of phenothiazine were added to each of two chemical tanks among them. Nitrogen gas was blown into each chemical tank with stirring for 20 minutes, then argon gas was blown into each tank for 20 seconds, and each chemical tank was hermetically closed. Each chemical tank was maintained in a thermostatic chamber at 40° C. for four months, then opened, and analyzed. It was observed that propylene glycol monosorbate charged in both of two chemical tanks was satisfactorily maintained without changes of the purity, the Hazen standard and the viscosity.

COMPARATIVE EXAMPLE 1

Two remaining chemical tanks charged with propylene glycol monosorbate in Example 1 were used. A chemical tank among them was maintained under the same conditions as in Example 1 except that it was not treated under an inert atmosphere, and the propylene glycol monosorbate obtained was analyzed. It was observed that the propylene glycol monosorbate was maintained without change of the Hazen standard. However, the purity was below 90% and the viscosity increased to approximately 600 cp at 20° C.

The other chemical tank was maintained under the same conditions as in Example 1 except that 2,6-di-t-butyl-p-cresol and phenothiazine was not added and then the propylene glycol monosorbate obtained was analyzed. The viscosity increased to about 8000 cp.

COMPARATIVE EXAMPLE 2

Using the same method as in Example 1 except that phenothiazine was not added. The yield of propylene glycol monosorbate was lowered to about 88% (60.1 kg).

EXAMPLE 2

Using the same method as in Example 1 except that ferric sorbate was changed to 0.65 kg of ferric chloride, 61.8 kg of propylene glycol monosorbate (a mixture of 2-hydroxypropyl sorbate and 2-hydroxy-1-methylethyl sorbate) having a purity of over 99%, a Hazen platinum-cobalt standard (APHA) of less than 20 and a viscosity of 60 cp at 20° C. was obtained.

The yield of the isolated propylene glycol monosorbate based on the starting sorbic acid was 91%.

Four chemical tanks were charged with 15 kg of the isolated propylene glycol monosorbate, respectively. Two chemical tanks among them were maintained in the same method as in Example 1. It was observed that propylene glycol monosorbate charged in both of them was maintained without any change of the quality for three months.

15 g (1000 ppm) of 2,6-di-t-butyl-p-cresol was added to one of the remaining chemical tanks (each tank was charged with 15 kg of propylene glycol monosorbate) and 1.5 g (100 ppm) of phenothiazine was added to the other chemical tank. After each chemical tank was treated under an inert atmosphere by using the same method as in Example 1 and hermetically closed, each tank was maintained at 40° C. These tanks were maintained without any change of the quality of propylene glycol monosorbate for three months.

EXAMPLE 3

Both of the washed water containing ferric hydroxide and sodium sorbate solutions which were separated by washing the synthesized liquid with the aqueous solution of sodium carbonate in Examples 1 and 2 were mixed, and the mixture was separated by filtering into the precipitate of ferric hydroxide and the filtrate of sodium sorbate. The precipitate contained 38% of ferric hydroxide and 62% of water. After 1.4 kg of the precipitate, 5 kg of xylene and 2 kg of sorbic acid were charged in a catalyst preparing reactor, the mixture was heated at 60° C. with stirring and dehydrated by vacuum distillation to obtain ferric sorbate.

Using the same method as in Example 1 except that ferric sorbate obtained by the above and 0.7 kg of sorbic acid which remained without reacting in the above process for producing ferric sorbate were charged in a reactor, 63.3 kg of propylene glycol monosorbate was obtained.

Each of four tanks was charged with the obtained propylene glycol monosorbate by using the same method as in Example 1 and maintained. These tanks were maintained without any change of the quality of the compound for over four months.

EXAMPLE 4

The washed water containing ferric hydroxide and sodium sorbate solutions which were separated by washing the synthesized liquid with the aqueous solution of sodium carbonate in Example 3 was separated into a solid phase and a liquid phase. The precipitate of ferric hydroxide which was contained in the solid phase was dissolved in hydrochloric acid. The solution obtained and the filtrate containing sodium sorbate in the liquid phase were mixed with stirring. When the pH of the mixture was adjusted to about 7, ferric sorbate was precipitated. The precipitate was filtered with a centrifuge. The purity of the obtained water-containing ferric sorbate was 41%. An amount of 4.0 kg of the obtained ferric sorbate was charged in a reactor for synthesizing.

Then, 50.5 kg of water-containing sorbic acid having the purity of 89% and 50 kg of toluene which was recovered by film distillation was charged in the reactor and the mixture was heated at a set temperature of 92° C. with stirring to remove water. After observing that water was distilled away, the set temperature was changed to 80° C., 24.5 kg of liquid propylene oxide was fed to the reactor at a rate of 180 ml/min and propylene glycol monosorbate (a mixture of 2-hydroxypropyl sorbate and 2-hydroxy-1-methylethyl sorbate) was synthesized.

The synthesized liquid was washed by using 3.5 kg of sodium carbonate dissolved in 50 liters of filtrate which was recovered at the time of production of ferric sorbate and ferric sorbate and the like were separated.

Then, the toluene phase obtained was passed through a filter and fed to a film vacuum-distilling device having two columns, continuously. Toluene was recovered at the first column and 64.9 kg of propylene glycol monosorbate was obtained at the second column. The obtained propylene glycol monosorbate (a mixture of 2-hydroxypropyl sorbate and 2-hydroxy-1-methylethyl sorbate) had a purity of over 99%, a Hazen platinum-cobalt standard (APHA) of under 20 and a viscosity of 60 cp (25° C.) and it was good in quality.

Three chemical tanks of 20 liters were charged with 20 kg of the propylene glycol monosorbate obtained, respectively. An amount 10 g (500 ppm) of 2,6-di-t-butyl-p-cresol and 2 g (100 ppm) of phenothiazine were added to each chemical tank and the mixture was stirred with blowing nitrogen gas for 30 minutes.

Further, argon gas was blown into each chemical tank so as to remove the contained nitrogen gas and each chemical tank was hermetically closed. It was observed that propylene glycol monosorbate charged in the chemical tanks was maintained without any change in quality for a year.

COMPARATIVE EXAMPLE 3

Using the same method as in Example 4 except that the synthesized liquid was not washed by using an aqueous solution of sodium carbonate, 59.4 kg of propylene glycol monosorbate was obtained.

At the latter half of the process of distillation, it was observed that the heat transfer surface was soiled and that a small amount of propylene glycol monosorbate was contained in the high-boiling materials. However, the propylene glycol monosorbate obtained had a purity of over 99%, a Hazen platinum-cobalt standard (APHA) of 25 and a viscosity of 60 cp (25° C.) and it had almost the same appearance as that obtained in Example 3. However, when the propylene glycol monosorbate obtained was maintained by the same method as described in Example 4, the purity was lowered to 92% and the viscosity was increased to 1200 cp.

EXAMPLE 5

Using the same method as in Example 1 except that propylene oxide was changed to 30.4 kg of 1,2-butylene oxide and the synthesis temperature was changed to 90° C., butanediol monosorbate was synthesized. After the synthesized liquid was washed in an aqueous solution of sodium carbonate, the washed liquid was purified by distilling at a film-distilling temperature 10° C. higher than that in Example 1. An amount of 69.9 kg of 1,2-butanediol monosorbate (a mixture of 2-hydroxybutyl sorbate and 2-hydroxy-1-ethylethyl sorbate) having a purity of over 99%, a Hazen platinum-cobalt standard (APHA) of under 20 and a viscosity of 70 cp (20° C.) was obtained (yield: 93%). Three chemical tanks of 20 liters were charged with 20 kg of the obtained 1,2-butanediol monosorbate, respectively. Inert gas was blown into these chemical tanks under the same conditions as in Example 1, and 2,6-di-t-butyl-p-cresol and phenothiazine were added. The chemical tanks were hermetically closed and maintained at 40° C. It was observed that 1,2-butanediol monosorbate in these tanks was maintained without any change for four months.

EXAMPLE 6

Using the same method as in Example 5 except that 1,2-butylene oxide was changed to 2,3-butylene oxide, 69.2 kg of purified butylene glycol monosorbate (a mixture of 2-hydroxy-1-dimethylethyl sorbate and 2-hydroxy-2-methyl propyl sorbate) having a purity of over 99%, a Hazen platinum-cobalt standard (APHA) of under 20 and a viscosity of 70 cp (20° C.) was obtained (yield: 94%). Four chemical tanks of 20 liters were charged with 15 kg of the obtained sorbate, respectively. Inert gas was blown into these chemical tanks, and 1.5 g of phenothiazine was added. The chemical tanks were hermetically closed and maintained at room temperature. It was observed that 2-hydroxy-1-methylpropyl sorbate in these tanks were maintained without any change for six months.

We claim:

1. A method of producing an alkylene glycol monosorbate, which comprises (a) reacting sorbic acid and an alkylene oxide having 2 to 4 carbon atoms in a system containing a solvent having a boiling point of 150° C. or less at atmospheric pressure and being insoluble or slightly soluble in water and being inactive to the alkylene glycol monosorbate in the presence of one or more catalysts selected from the group consisting of organic acid iron salts and iron halides and one or more compounds selected from the group consisting of phenothiazines and alkylphenols, (b) washing the obtained synthesized liquid with an aqueous solution of a salt selected from the group consisting of sodium carbonate, potassium carbonate, sodium bicarbonate and potassium bicarbonate, and then (c) purifying the washed liquid by distillation.

2. A method as claimed in claim 1, wherein the catalyst is sorbic acid iron salt.

3. A method as claimed in claim 2, wherein the catalyst is obtained by stirring and mixing the solvent, sorbic acid and iron hydroxide in the presence of water, and then dehydrating the obtained mixture.

4. A method as claimed in claim 1, wherein the catalyst is repeatedly used by recovering the solution containing iron hydroxide and sorbates which is separated from the liquid by washing with the aqueous solution of the salt selected from the group consisting of sodium carbonate, potassium carbonate, sodium bicarbonate and potassium bicarbonate, and then synthesizing sorbic acid iron salt by reacting the recovered solution and sulfuric acid or hydrochloric acid.

5. A method of preserving an alkylene glycol monosorbate, which comprises adding one or more compounds selected from the group consisting of alkylphenols and phenothiazines to the alkylene glycol monosorbate and stirring to mix them, removing oxygen from a vessel containing the mixture, and sealing hermetically the vessel.

* * * * *